(12) United States Patent
Mori et al.

(10) Patent No.: US 8,080,143 B2
(45) Date of Patent: Dec. 20, 2011

(54) GAS SENSOR ELEMENT, METHOD FOR MANUFACTURING THE SAME, AND GAS SENSOR

(75) Inventors: Shigeki Mori, Gifu (JP); Masaki Mizutani, Aichi (JP); Akinori Kojima, Aichi (JP); Shigeo Kondo, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 1121 days.

(21) Appl. No.: 11/392,574

(22) Filed: Mar. 30, 2006

(65) Prior Publication Data

US 2006/0219554 A1    Oct. 5, 2006

(30) Foreign Application Priority Data

Mar. 31, 2005  (JP) ................................. 2005-100425

(51) Int. Cl.
*G01N 27/407*   (2006.01)
*G01N 27/409*   (2006.01)

(52) U.S. Cl. ..................... 204/424; 205/784; 156/89.11; 156/261

(58) Field of Classification Search .................. 204/424, 204/428, 426, 410, 412, 425; 205/781, 784, 205/788; 73/23.31; 156/89.11–89.16, 250, 156/261
See application file for complete search history.

(56) References Cited

U.S. PATENT DOCUMENTS

| 630,677 | A | * | 8/1899 | Vargo et al. ...................... 44/597 |
| 4,574,445 | A | * | 3/1986 | Bentin et al. .................. 29/890.1 |
| 6,306,677 | B1 | | 10/2001 | Vargo et al. |
| 6,344,134 | B1 | * | 2/2002 | Yamada et al. ............... 205/781 |

FOREIGN PATENT DOCUMENTS

| GB | 2200460 | * | 8/1988 |
| JP | 2003-294687 | | 10/2003 |

* cited by examiner

*Primary Examiner* — Alex Noguerola
*Assistant Examiner* — Gurpreet Kaur
(74) *Attorney, Agent, or Firm* — Sughrue Mion, PLLC

(57) ABSTRACT

A method for manufacturing a gas sensor element (300), which includes a plate-like second solid electrolyte member (109), a fourth electrode (110) formed on the second solid electrolyte member (109), and a protection layer (111) including a reinforcement member (112) having an insertion hole (112a), and a porous electrode protection member (113a) provided in the insertion hole (112) and adapted to protect the fourth electrode (110) from becoming poisoned. The method includes a pressing step of, after disposing a green electrode protection member (113a) in the insertion hole (112a) of a green reinforcement member (112), pressing at least one of the green reinforcement member (112) and the green electrode protection member (113a) so as to form a green protection layer (111); a laminate-forming step of arranging the green protection layer (111) and a green solid electrolyte member (113a) in layers so as to form a laminate which will become the gas sensor element (300) after being fired; and a firing step of firing the laminate.

5 Claims, 9 Drawing Sheets

GAS SENSOR ELEMENT, METHOD FOR MANUFACTURING THE SAME, AND GAS SENSOR

BACKGROUND OF THE INVENTION

1. Field of the Invention

The present invention relates to a gas sensor element, a method for manufacturing the same, and a gas sensor.

2. Description of the Related Art

A conventional gas sensor is disclosed in Patent Document 1. The gas sensor includes an axially extending gas sensor element for detecting at its front end portion a gas to be measured, a heater for activating the gas sensor element, and a metallic shell for supporting the gas sensor element.

The gas sensor element and the heater have the structure shown in FIG. 11. FIG. 11 is an exploded perspective view of the gas sensor element and the heater. Specifically, the structure is a multilayer structure in which, mainly, a first substrate 101, a heating member 102, a second substrate 103, a first electrode 104, a first solid electrolyte member 105, a second electrode 106, an insulation layer 107, a third electrode 108, a second solid electrolyte member 109, a fourth electrode 110, and a protection layer 111 are sequentially arranged in layers. The protection layer 111 includes a reinforcement member 112 having an insertion hole 112a which extends therethrough in the laminating direction, and an electrode protection member 113a inserted into the insertion hole 112a. The reinforcement member 112 prevents warpage and enhances the strength of a gas sensor element 300 and a heater 200. The electrode protection member 113a is a porous member which protects the fourth electrode 110 (specifically, a fourth electrode portion 110a) from becoming poisoned while maintaining gas communication between the fourth electrode 110 and the atmosphere.

The gas sensor is manufactured as follows. First, a green electrode protection member 113a, which is the electrode protection member 113a before firing, is inserted into the insertion hole 112a of a green reinforcement member 112, which is the reinforcement member 112 before firing. A green protection layer 111 is thus formed, which is the protection layer 111 before firing. Subsequently, a first green substrate 101, which is the first substrate 101 before firing, a first green solid electrolyte member 105, which is the first solid electrolyte member 105 before firing, a second green solid electrolyte member 109, which is the second solid electrolyte member 109 before firing, and the like, together with the green protection layer 111, are arranged in layers, thereby yielding a laminate. Next, the laminate is subjected to resin removal firing, and then main firing, whereby the gas sensor element 300 and the heater 200 are obtained in an integrated fashion. Then, the gas sensor element 300 and the heater 200 are attached to a metallic shell and the like, thereby yielding a gas sensor.

The thus-obtained gas sensor is attached to, for example, an exhaust system such as an exhaust pipe of an engine and is used to detect a gas to be measured which is contained in exhaust gas.

[Patent Document 1] Japanese Patent Application Laid-Open (kokai) No. 2003-294687

3. Problems to be Solved by the Invention

The above-mentioned conventional gas sensors are at risk of increased variation in gas detection performance among respective sensors. Consequently, in some cases, yield has been insufficient.

Specifically, as shown in FIG. 13, the present inventors have found that, in the gas sensor element, a crack CR tends to occur in the second solid electrolyte member 109, which is formed from the second green solid electrolyte member 109 by firing. Gas sensors having the crack CR are at risk of increased variation in gas detection performance among respective sensors. Thus, in some cases, production yield has been insufficient. This is because even when other requirements are satisfied, occurrence of the crack CR causes a reduction in electric potential between the electrodes developed by a gas to be measured.

The present invention has been accomplished in view of the foregoing, and an object of the present invention is to reduce variation in gas detection performance among gas sensors and to enable manufacture of gas sensors at high yield.

SUMMARY OF THE INVENTION

The present inventors found that crack CR in the second solid electrolyte member 109 is caused by a gap G between the reinforcement member 112 and the electrode protection member 113a in the protection layer 111; more precisely, the gap G between the green reinforcement member 112 and the green electrode protection member 113a in the green protection layer 111. In other words, when, in the firing step (particularly at the time of resin removal), a gap G is present between the green electrode protection member 113a and the wall surface of the insertion hole 112a of the green reinforcement member 112, stress is likely to concentrate on a portion around the gap G in the second green solid electrolyte member during firing. This is due to a difference in shrinkage rate between the second green solid electrolyte member 109 and that of the green reinforcement member 112 and the green electrode protection member 113a. As a result, the crack CR occurs in the second solid electrolyte member 109 around the gap G. On the basis of this finding, the present inventors have completed the invention.

The present invention provides a method for manufacturing a gas sensor element comprising a solid electrolyte member, an electrode formed on the solid electrolyte member, and a protection layer including a reinforcement member having an insertion hole, and a porous electrode protection member provided in the insertion hole and adapted to protect the electrode from becoming poisoned. The method comprises a pressing step of, after disposing a green electrode protection member in the insertion hole of a green reinforcement member, pressing at least one of the green reinforcement member and the green electrode protection member so as to form a green protection layer; a laminate-forming step of arranging the green protection layer and a green solid electrolyte member in layers so as to form a laminate which will become the gas sensor element after being fired; and a firing step of firing the laminate.

In the manufacturing method of the present invention, during the pressing step at least one of the green reinforcement member and the green electrode protection member is pressed. Accordingly, the green reinforcement member or the green electrode protection member is pressed into a gap between the green electrode protection member and the wall surface of the insertion hole. In the resultant laminate, a gap is unlikely to arise between the green reinforcement member and the green electrode protection member, thereby providing enhanced adhesion. Therefore, when the laminate is fired, thermal shrinkage of the green solid electrolyte member into the solid electrolyte member is unlikely to be influenced by an atmosphere which would otherwise be present in the gap arising in a conventional manufacturing method. Thus, the solid electrolyte member is unlikely to crack.

Accordingly, the thus-obtained gas sensor is free from reduction in electric potential between the electrodes developed by a gas to be measured, and exhibits reduced variation in gas detection performance among respective sensors. Furthermore, gas sensors exhibiting the above characteristics can be manufactured at high yield.

Thus, the method for manufacturing a gas sensor element of the present invention can reduce variation in gas detection performance among respective gas sensors, and can provide such gas sensors at high yield.

Preferably, in the manufacturing method of the present invention, the pressing step is performed at room temperature (20° C.) or higher, preferably 40° C. or higher. This enhances fluidity of the green reinforcement member and the green electrode protection member of the green protection layer, so that the green reinforcement member and/or the green electrode protection member can be more readily pressed into the gap. Thus, the gap can be filled more reliably, the pressing time can be shortened, and the applied pressure can be reduced.

Preferably, in the manufacturing method of the present invention, the green electrode protection member is pressed. Generally, because the green electrode protection member is smaller than the green reinforcement member in terms of area perpendicular to the laminating direction, the green electrode protection member is more likely to expand outwardly under pressure. Also, since the green electrode protection member expands outwardly through application of pressure so as to fit the insertion hole of the green reinforcement member whose dimensions are fixed, dimensional accuracy can be ensured.

Preferably, in the case where the green electrode protection member is pressed, before the pressing step is performed, the thickness of the green electrode protection member is greater than that of the green reinforcement member. This allows the green electrode protection member to readily expand outwardly under pressure without influencing the green reinforcement member. In this case, preferably, after the pressing step, the green reinforcement member and the green electrode protection member have substantially the same thickness.

Preferably, in the manufacturing method of the present invention, even when the green electrode protection member is thicker than the green reinforcement member with respect to the laminating direction, or the green reinforcement member is thicker than the green electrode protection member with respect to the laminating direction, the reinforcement member and the electrode protection member have substantially the same thickness after firing. This is because, if the reinforcement member and the electrode protection member fail to have substantially the same thickness, the electric potential developed between the electrodes by a gas to be measured is reduced. As a result, gas detection performance is likely to vary among gas sensors.

Preferably, in the manufacturing method of the present invention, the insertion hole does not have a sharp corner as viewed in plane. Specifically, a polygonal shape having rounded corners, a circular shape, or the like is preferred. The use of such a shape makes a gap less prone to arise between the green reinforcement member and the green electrode protection member. Particularly, when the electrode protection member formed through firing while being fitted in the insertion hole in a gapless condition does not have a sharp corner as viewed in the laminating direction, thermal strength and mechanical strength are enhanced.

A gas sensor element of the present invention comprises a solid electrolyte member having a plate-like shape; an electrode formed on the solid electrolyte member; and a protection layer including a reinforcement member having an insertion hole, and a porous electrode protection member provided in the insertion hole and adapted to protect the electrode from becoming poisoned. In the gas sensor element, a gap in excess of an average diameter of pores in the electrode protection member is absent between an inner peripheral surface of the insertion hole and an outer peripheral surface of the electrode protection member.

When a gap between the inner peripheral surface of the insertion hole and the outer peripheral surface of the electrode protection member is not greater than the average diameter of pores in the electrode protection member, initiation of a crack in the solid electrolyte member can be prevented. Conceivably, the reason is as follows. If a gap is unlikely to arise between the wall surface of the insertion hole and the green protection member, which is the electrode protection member before firing, in the firing step, thermal shrinkage of the green solid electrolyte member during firing (to thereby form the solid electrolyte member) is unlikely to be influenced by an atmosphere which would otherwise be present in the gap arising in a conventional manufacturing method.

Accordingly, gas sensors which employ the gas sensor element of the present invention exhibit reduced variation in gas detection performance among the respective sensors, and can be manufactured at high yield.

A gas sensor of the present invention comprises a gas sensor element for detecting a gas to be measured, and a metallic shell for supporting the gas sensor element. The gas sensor employs the above-described gas sensor element.

The gas sensors exhibit reduced variation in gas detection performance among the respective sensors, and can be manufactured at high yield.

The present invention provides a method for manufacturing a gas sensor element comprising a solid electrolyte member having a plate-like shape, an electrode formed on the solid electrolyte member, and a protection layer including a reinforcement member having an insertion hole, and a porous electrode protection member provided in the insertion hole and adapted to protect the electrode from becoming poisoned. The manufacturing method comprises an insertion-hole-forming step of punching the insertion hole in a first green ceramic sheet so as to form a green reinforcement member having the insertion hole; a blanking step of blanking out a blank from a second green ceramic sheet placed on the green reinforcement member so as to dispose the blank as a green electrode protection member in the insertion hole of the green reinforcement member; and a firing step of firing the green reinforcement member and the green electrode protection member so as to form the reinforcement member and the electrode protection member.

As mentioned above, the blank which is blanked out from the second green ceramic sheet is disposed in the insertion hole of the green reinforcement member as a green electrode protection member, to thereby prevent formation of a gap between the green electrode protection member and the wall surface of the insertion hole to the extent possible. Also, a step of blanking out the green electrode protection member from the second green ceramic sheet and a step of disposing the obtained green electrode protection member in the insertion hole can be performed simultaneously, thereby reducing the number of processing steps.

Preferably, the manufacturing method of the present invention further comprises a pressing step of, after the blanking step, pressing at least one of the green reinforcement member and the green electrode protection member so as to form a green protection layer. Such pressing deforms the pressed green reinforcement member or the pressed green electrode protection member so as to fill a gap between the green electrode protection member and the wall surface of the insertion hole, thereby improving adhesion therebetween. Therefore, when the resultant laminate is fired, thermal shrinkage of the green solid electrolyte member is unlikely to be influenced by an atmosphere which would otherwise be present in the gap arising in a conventional manufacturing method, so that the solid electrolyte member is unlikely to crack.

DESCRIPTION OF REFERENCE NUMERALS

Figure 1:
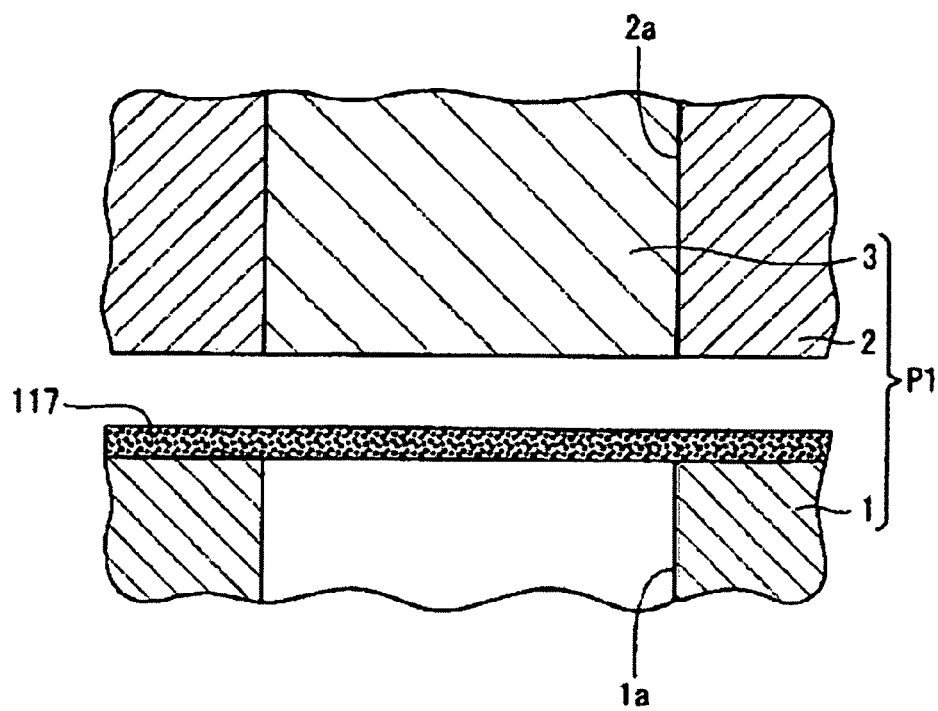
FIG. 1 is a schematic enlarged sectional view relating to Embodiment 1 and showing a forming die for cutting an insertion hole through a green reinforcement member.

Reference numerals used to identify various structural features in the drawings include the following.
109 . . . second solid electrolyte member, second green solid electrolyte member
405 . . . second solid electrolyte member
111 . . . protection layer, green protection layer
407 . . . protection layer
110 . . . fourth electrode, fourth green electrode
406 . . . fourth electrode
300, 600 . . . gas sensor element
112a . . . insertion hole
112 . . . reinforcement member, green reinforcement member
113 . . . second green ceramic sheet
117 . . . first green ceramic sheet
408 . . . reinforcement member
113a . . . electrode protection member, green electrode protection member
409a . . . electrode protection member G . . . gap
23 . . . metallic shell

DETAILED DESCRIPTION OF THE PREFERRED EMBODIMENTS

Embodiments 1 and 2 of the present invention will next be described with reference to the drawings. However, the present invention should not be construed as being limited thereto.

Embodiment 1

First, a gas sensor of Embodiment 1 will be described.

Figure 9:
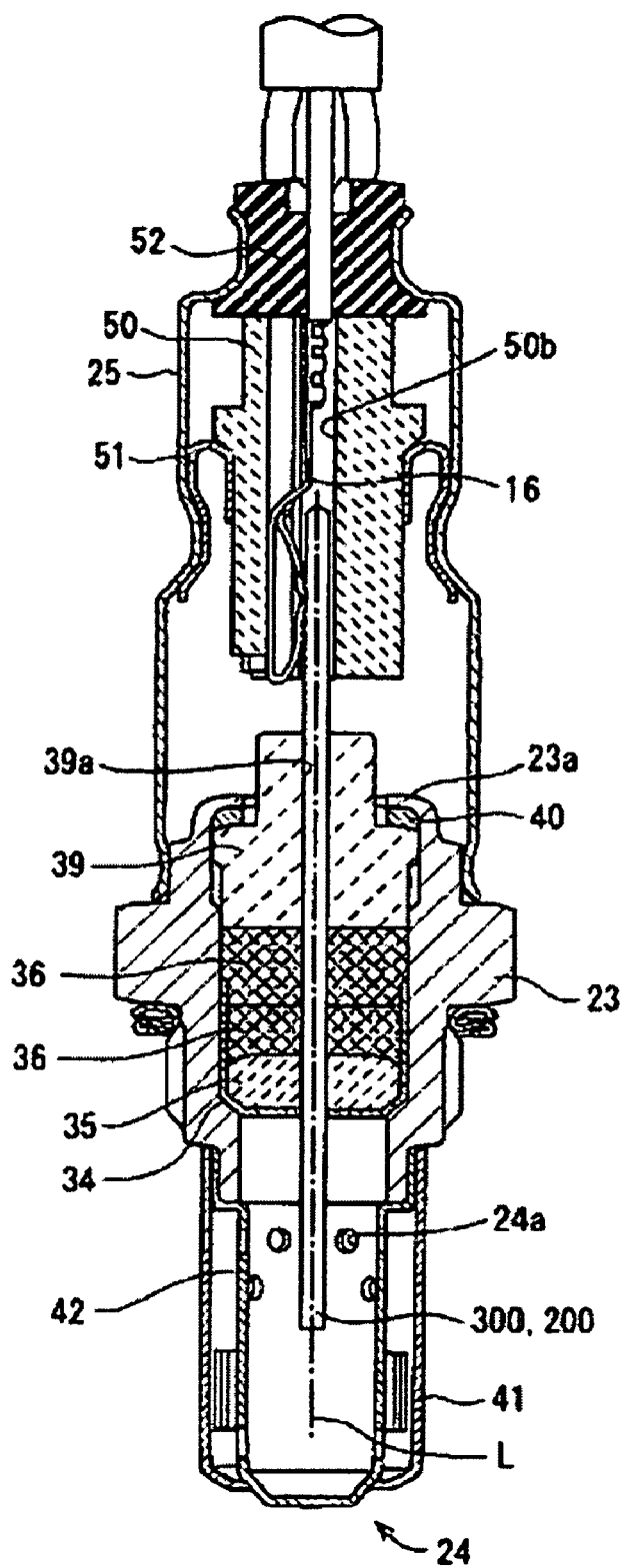
FIG. 9 is a sectional view of a gas sensor according to Embodiments 1 and 2.

As shown in FIG. 9, the gas sensor includes a gas sensor element 300; a heater 200 laminated on the gas sensor element 300; a metallic shell 23 which retains the gas sensor element 300 and the like therein; and a protector 24 attached to a front end portion of the metallic shell 23. The gas sensor element 300 and the heater 200 are disposed so as to extend in the direction of an axis L.

Figure 11:
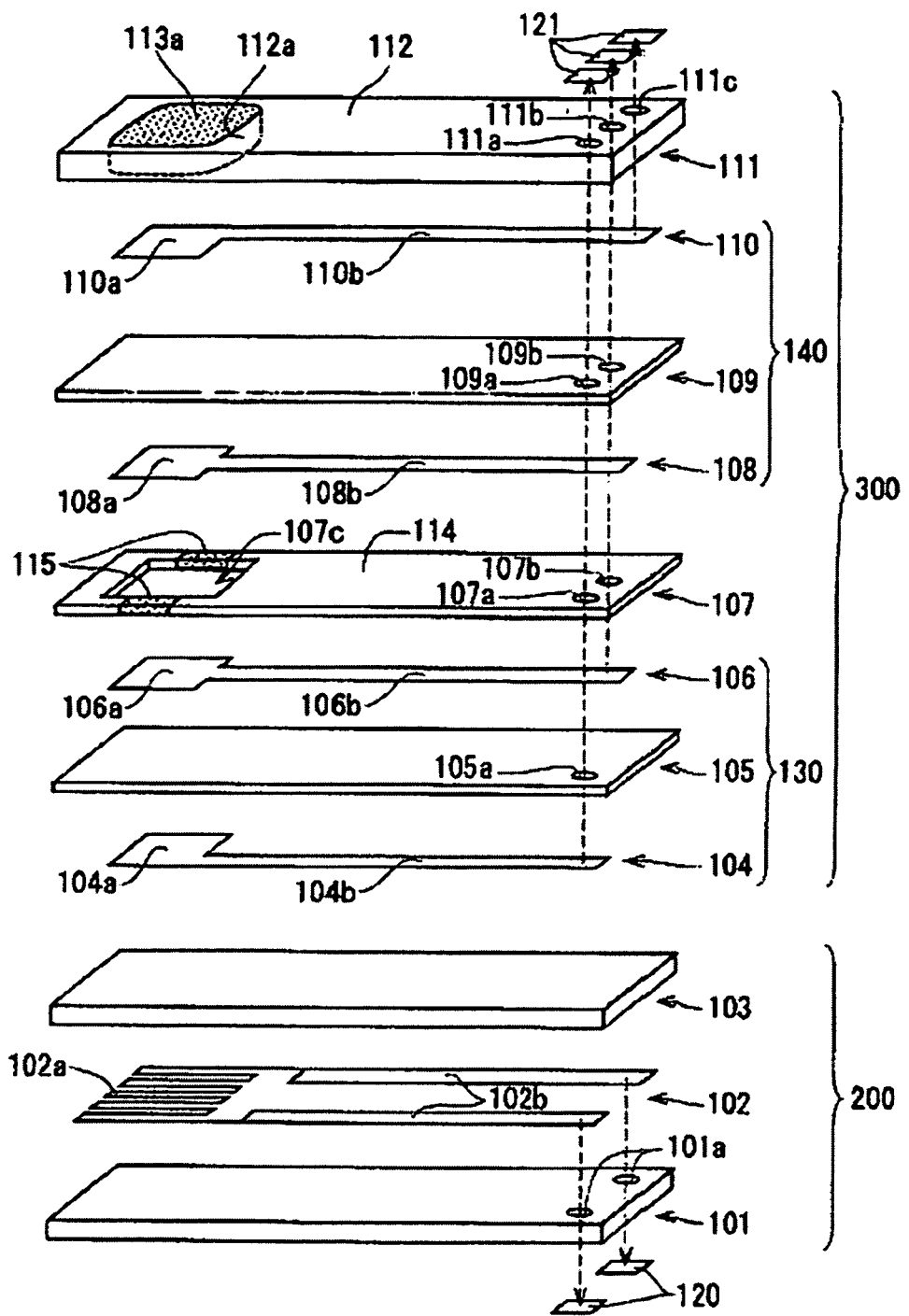
FIG. 11 is a schematic exploded perspective view of a gas sensor element and a heater, relating to both Embodiment 1 and a conventional design.

As shown in FIG. 11, the heater 200 includes a first substrate 101, a second substrate 103, and a heating member 102. The first and second substrates 101 and 103 predominantly contain alumina. The heating member 102 includes a heating portion 102a located on the front-end side thereof, and a pair of heater lead portions 102b. Ends of the heater lead portions 102b are electrically connected to corresponding heater-side pads 120 via corresponding through holes 101a formed in the first substrate 101.

The gas sensor element 300 includes an oxygen concentration detection cell 130 and an oxygen pump cell 140. The oxygen concentration detection cell 130 includes a first solid electrolyte member 105, a first electrode 104, and a second electrode 106. The first and second electrodes 104 and 106 are formed on corresponding opposite sides of the first solid electrolyte member 105. The first electrode 104 includes a first electrode portion 104a and a first lead portion 104b. The second electrode 106 includes a second electrode portion 106a and a second lead portion 106b.

An end of the first lead portion 104b is electrically connected to a corresponding gas-sensor-element-side pad 121 via a through hole 105a, a through hole 107a, a through hole 109a, and a through hole 111a. An end of the second lead portion 106b is electrically connected to a corresponding gas-sensor-element-side pad 121 via a through hole 107b, a through hole 109b, and a through hole 111b.

The oxygen pump cell 140 includes a second solid electrolyte member 109, a third electrode 108, and a fourth electrode 110. The third and fourth electrodes 108 and 110 are formed on corresponding opposite sides of the second solid electrolyte member 109. The third electrode 108 includes a third electrode portion 108a and a third lead portion 108b. The fourth electrode 110 includes a fourth electrode portion 110a and a fourth lead portion 110b.

An end of the third lead portion 108b is electrically connected to a corresponding gas-sensor-element-side pad 121 via the through hole 109b and the through hole 111b. An end of the fourth lead portion 110b is electrically connected to a corresponding gas-sensor-element-side pad 121 via a through hole 111c. The second lead portion 106b and the third lead portion 108b have the same electric potential via the through hole 107b.

The first solid electrolyte member 105 and the second solid electrolyte member 109 are made of a partially-stabilizedzirconia sintered body which is formed by adding yttria ($Y_2O_3$) or calcia (CaO) serving as a stabilizer to zirconia ($ZrO_2$).

The heating member 102, the first electrode 104, the second electrode 106, the third electrode 108, the fourth electrode 110, the heater-side pads 120, and the gas-sensor-element-side pads 121 can be formed from a platinum group element. Platinum group elements which are preferred for forming the members include Pt, Rh, and Pd. These elements can be used singly or in combination.

More preferably, in view of heat resistance and oxidation resistance, Pt is predominantly used to form the heating member 102, the first electrode 104, the second electrode 106, the third electrode 108, the fourth electrode 110, the heater-side pads 120, and the gas-sensor-element-side pads 121. Further preferably, the heating member 102, the first electrode 104, the second electrode 106, the third electrode 108, the fourth electrode 110, the heater-side pads 120, and the gas-sensor-element-side pads 121 contain a ceramic component in addition to a platinum group element (main component). Preferably, to promote adhesion, the ceramic component is similar to a material which is predominantly contained in a counterpart of the laminate (e.g., a main component of the first solid electrolyte member 105 and the second solid electrolyte member 109).

An insulation layer 107 is formed between the oxygen pump cell 140 and the oxygen concentration detection cell 130. The insulation layer 107 includes an insulation portion 114 and diffusion-controlling portions 115. A gas detection chamber 107c is formed in the insulation portion 114 of the insulation layer 107 at a position corresponding to the second electrode portion 106a and the third electrode portion 108a. The gas detection chamber 107c communicates with the outside along the lateral direction of the insulation layer 107. In the communication region of the insulation layer 107, the diffusion-controlling portions 115 are provided so as to implement gas diffusion at a predetermined flow rate between the outside and the gas detection chamber 107c.

No particular limitation is imposed on the insulation portion 114, so long as the insulation portion 114 is made of an electrically insulative ceramic sintered body. Examples of such a ceramic sintered body include oxide ceramics, such as alumina and mullite.

The diffusion-controlling portions 115 are made of a porous body of alumina. The diffusion-controlling portions 115 control the flow rate of a gas to be detected when the gas flows into the gas detection chamber 107c.

A protection layer 111 is formed on the surface of the second solid electrolyte member 109 such that the fourth electrode 110 is sandwiched therebetween. The protection layer 111 includes a porous electrode protection member 113a and a reinforcement member 112. The electrode protection member 113a covers the fourth electrode portion 110a so as to protect the fourth electrode portion 110a from becoming poisoned. The reinforcement member 112 protects the second solid electrolyte member 109 with the fourth lead portion 110b sandwiched therebetween.

Referring back to FIG. 9, a metal holder 34, a ceramic holder 35, and talc 36, from the front-end side to the rear-end side, are disposed in the metallic shell 23. A sleeve 39 made of alumina is disposed on the rear side of the talc 36. The sleeve 39 is formed into a multi-stepped cylindrical shape. An axial hole 39a is formed in the sleeve 39 along the axis and allows the gas sensor element 300 and the heater 200 to extend therethrough. A rear-end crimp portion 23a of the metallic shell 23 is bent radially inward, thereby pressing the sleeve 39 toward the front end of the metallic shell 23 via a ring member 40 made of stainless steel.

A protector 24 made of metal and having a plurality of gas intake holes 24a is welded to the outer peripheral surface of a front end portion of the metallic shell 23 and covers a front end portion of the gas sensor element 300 projecting from the front end of the metallic shell 23. The protector 24 includes an outer protector 41 and an inner protector 42.

An external tube 25, a separator 50, and a retainer 51 are provided on the rear-end side of the metallic shell 23. Connection terminals for connecting lead wires and external terminals of the gas sensor element 300 and external terminals of the heater 200 are accommodated in through holes 50b of the separator 50. A rubber cap 52 is disposed on the rear-end side of the separator 50.

Next, a method used for manufacturing the gas sensor element of Embodiment 1 will be described.

First, a first material powder and a plasticizer were wet-mixed, thereby preparing a slurry in which the powder and the plasticizer were dispersed. The first material powder is composed of, for example, 97 wt % alumina powder, and 3 wt % silica serving as a sintering conditioner. The plasticizer is composed of a butyral resin and dibutyl phthalate (DBP). By a sheet-forming process which uses a doctor blade apparatus, the slurry was formed into a sheet having a thickness of 0.4 mm. The sheet was cut to a size of 140 mm×140 mm, thereby yielding a first green ceramic sheet 117 shown in FIG. 1.

Next, an insertion-hole-forming step was performed. First, a forming die P1 shown in FIGS. 1 and 2 was prepared. The forming die P1 includes a lower die 1, an upper die 2, and a punch 3. A working hole 1a of the lower die 1 and a working hole 2a of the upper die 2 have a square shape with rounded corners as viewed in a vertical direction. The punch 3 is arranged so as to be vertically movable through the working hole 2a and the working hole 1a.

Figure 2:
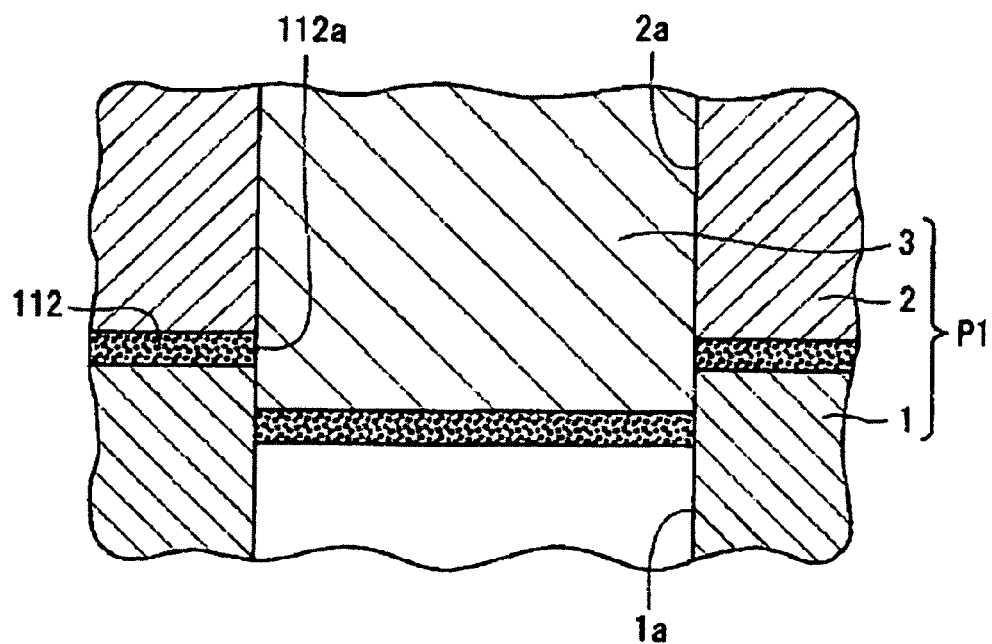
FIG. 2 is a schematic enlarged sectional view relating to Embodiment 1 and showing a state in which the forming die of FIG. 1 is closed.
Figure 3:
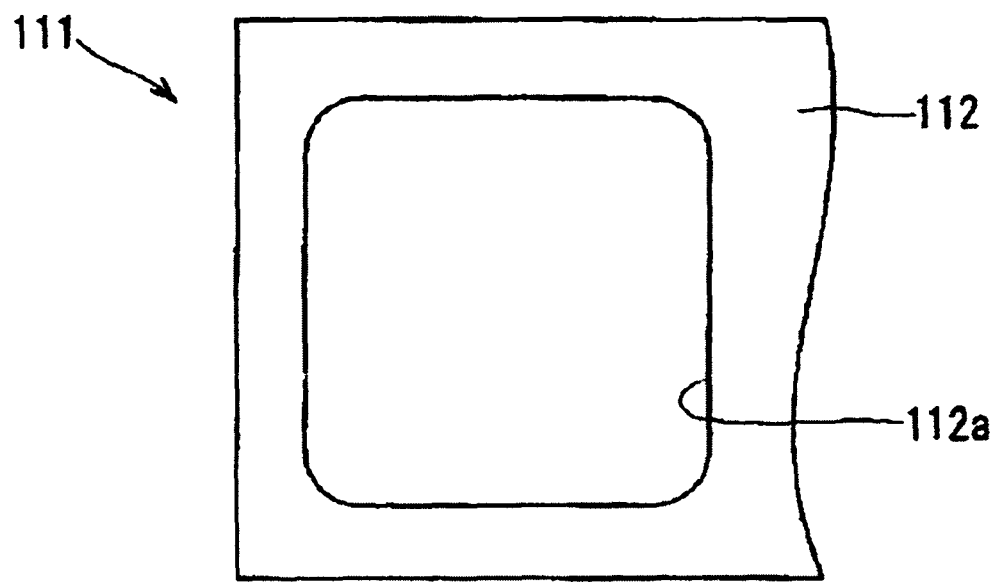
FIG. 3 is a plan view relating to Embodiment 1 and showing a green protection layer including the green reinforcement member and a green electrode protection member.

As shown in FIG. 1, the first green ceramic sheet 117 was placed on the lower die 1. As shown in FIG. 2, while the upper die 2 was lowered such that the first green ceramic sheet 117 was fixedly sandwiched between the upper die 2 and the lower die 1, the punch 3 was lowered so as to cut an insertion hole 112a through the first green ceramic sheet 117, thereby forming a green reinforcement member 112. As shown in FIG. 3, the insertion hole 112a has a square shape with rounded corners as viewed from above, as in the case of the working hole 1a.

Meanwhile, a second material powder and a plasticizer were wet-mixed, thereby preparing a slurry in which the powder and the plasticizer were dispersed. The second material powder is composed of, for example, 63 wt % alumina powder, 3 wt % silica serving as a sintering conditioner, and 34 wt % carbon powder. The plasticizer is composed of a butyral resin and DBP. As in the case of the green reinforcement member 112, by use of the slurry, a second green ceramic sheet 113 shown in FIG. 4 was obtained. The second green ceramic sheet 113 has a thickness of 0.4 mm+25 µm. Notably, the plasticizer was modified so as to increase extensibility of the second green ceramic sheet 113. In the present embodiment, the second green ceramic sheet 113 was formed with a thickness of 0.4 mm+25 µm. However, when the thickness is 0.4 mm+10 µm or greater, the green ceramic sheet 113 can fill a gap G in a pressing step, which will be described below.

Figure 4:
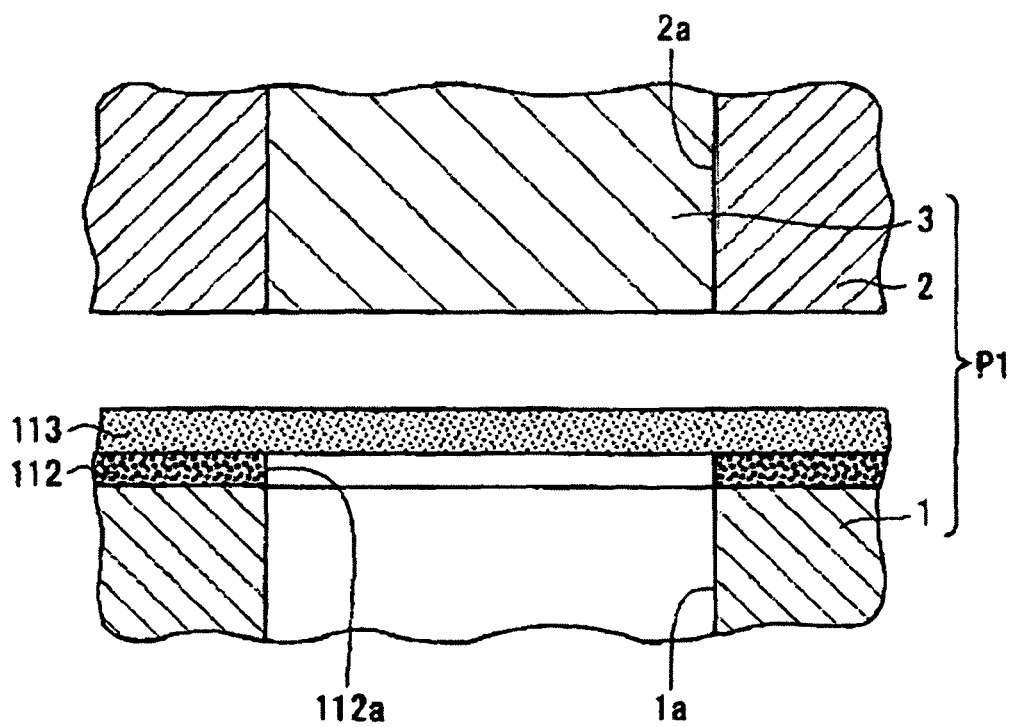
FIG. 4 is a schematic enlarged sectional view relating to Embodiment 1 and showing the forming die for inserting the green electrode protection member into the insertion hole of the green reinforcement member.
Figure 5:
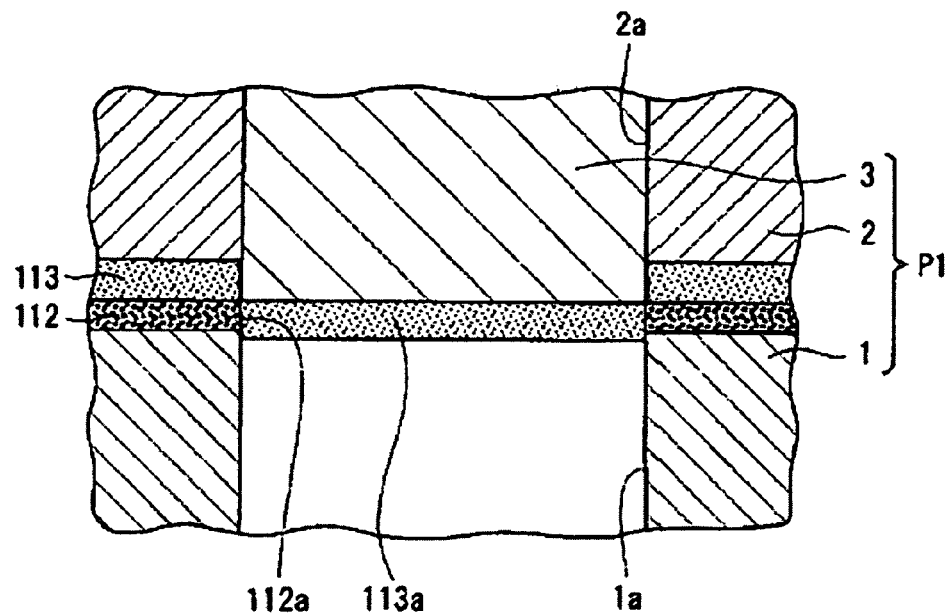
FIG. 5 is a schematic enlarged sectional view relating to Embodiment 1 and showing a state in which the forming die of FIG. 4 is closed.

Subsequently, a blanking step was performed. As shown in FIG. 4, the second green ceramic sheet 113 was placed on the green reinforcement member 112. As shown in FIG. 5, while the upper die 2 was lowered such that the green reinforcement member 112 and the second green ceramic sheet 113 were fixedly sandwiched between the upper die 2 and the lower die 1, the punch 3 was lowered so as to blank out a portion from the second green ceramic sheet 113, and the blanked-out portion was inserted into the insertion hole 112a to serve as a green electrode protection member 113a. In the present embodiment, after the punch 3 is lowered, the bottom surface of the punch 3 is at a vertical position aligned with the contact surface between the green reinforcement member 112 and the second green ceramic sheet 113. Notably, when the bottom surface of the lowered punch 3 is located below a position corresponding to half the thickness of the second green ceramic sheet 113, the green electrode protection member 113a can be sufficiently inserted into the insertion hole 112a of the green reinforcement member 112.

As described above, while the second green ceramic sheet 113 placed on the green reinforcement member 112 is subjected to blanking, the blanked-out green electrode protection member 113a is disposed in the insertion hole of the green reinforcement member 112, to thereby prevent formation of a gap between the green electrode protection member 113a and the wall surface of the insertion hole 112a to the extent possible. Also, a step of blanking out the green electrode protection member 113a from the green electrode protection sheet 113 and a step of disposing the green electrode protection member 113a thus obtained in the insertion hole 112a can be performed simultaneously and accurately.

Figure 6:
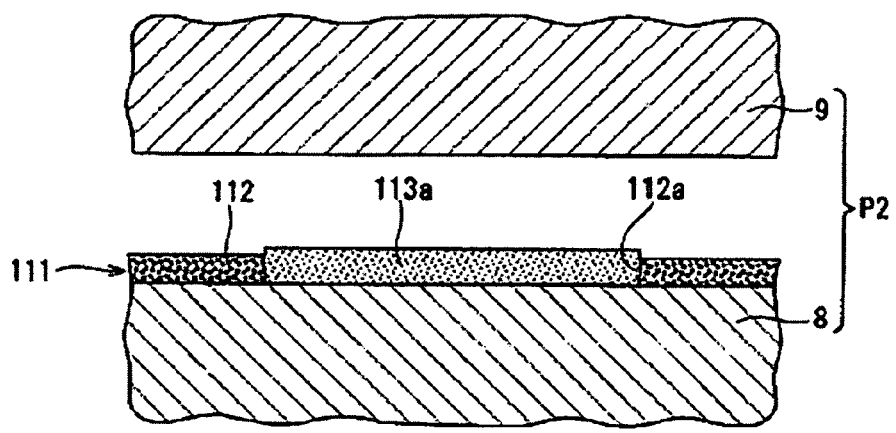
FIG. 6 is a schematic enlarged sectional view relating to Embodiment 1 and showing a forming die for pressing the green protection member.

Then, a pressing step is performed. As shown in FIG. 6, a forming die P2 was prepared. The forming die P2 includes a lower die 8 and an upper die 9. The top surface of the lower die 8 and the bottom surface of the upper die 9 are planar. An unillustrated heater is embedded in at least one of the lower die 8 and the upper die 9.

While heating the surface of the lower die 8 and the surface of the upper die 9 to 50° C. by the heater, a green protection layer 111 was disposed on the lower die 8. As measured in the direction of lamination before pressing, the green protection layer 111 is such that the green electrode protection member 113a is 25 µm thicker than the green reinforcement member 112.

Figure 7:
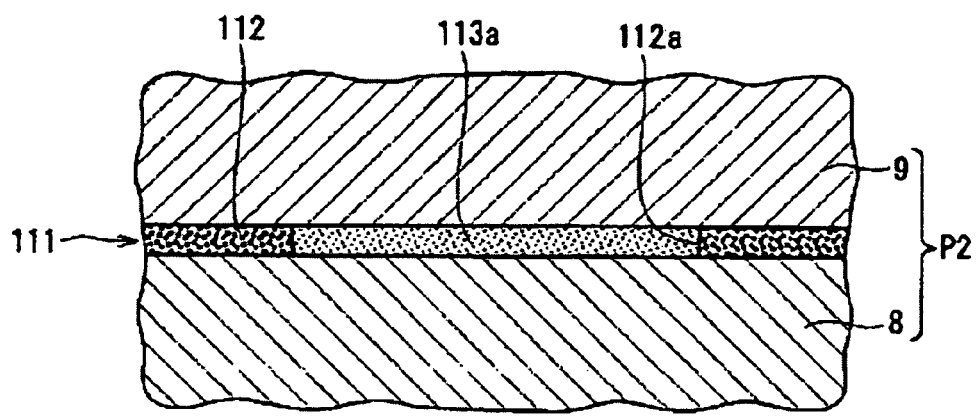
FIG. 7 is a schematic enlarged sectional view relating to Embodiment 1 and showing a state in which the forming die of FIG. 6 is closed.

Then, as shown in FIG. 7, the upper die 9 was lowered so as to press the green electrode protection member 113a downward at a pressure of 40 kg/cm$^2$. This causes the green electrode protection member 113a to expand into the gap G between the same and the wall surface of the insertion hole 112a of the green reinforcement member 112.

Figure 8:
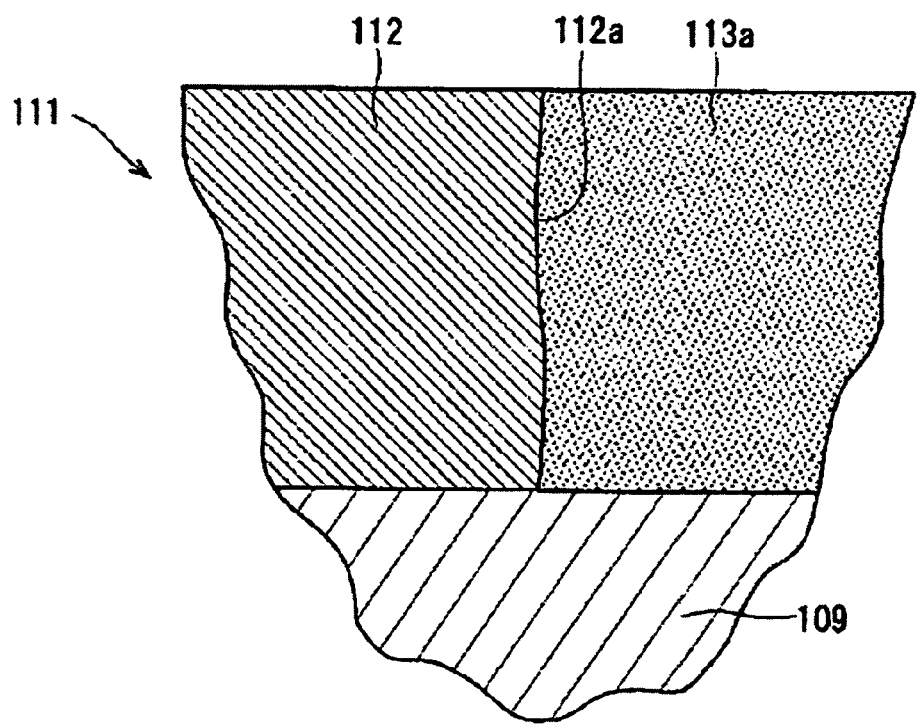
FIG. 8 is a schematic enlarged sectional view of a gas sensor element according to Embodiment 1.

Particularly, since the pressing step is performed while heating to room temperature or higher, the fluidity of the green electrode protection member 113a is increased, so that the green electrode protection member 113a is more readily pressed into the gap G. Thus, as shown in FIG. 8, the gap G can be filled more reliably; the pressing time can be shortened; and the applied pressure can be reduced. Since the shape of the insertion hole 112a of the green reinforcement member 112 as viewed in the laminating direction has no sharp corners, no gap remains at a corner. Further, since the green electrode protection member 113a, which is thicker than the green reinforcement member 112 as measured in the laminating direction and which is smaller than the green reinforcement member 112 in terms of surface area perpendicular to the laminating direction, is pressed, the green electrode protection member 113a can be readily press-spread. Also, since the green electrode protection member 113a is press-spread so as to be fitted to the insertion hole 112a of the green reinforcement member 112 whose dimensions are fixed, the dimensional accuracy of the insertion hole 112a can be maintained.

Subsequently, the upper die 9 was raised, and the green protection layer 111 was unloaded. The thus-obtained green protection layer 111 is such that the green reinforcement member 112 and the green electrode protection member 113a have substantially the same thickness.

Next, the laminating step will be described. In preparation for the laminating step, a first green substrate 101, a second green substrate 103, and a green insulation portion 114 of a green insulation layer 107 shown in FIG. 11 were prepared as in the case of the green ceramic sheet 117.

Further, a third material powder and a plasticizer were wet-mixed, thereby preparing a slurry in which the powder and the plasticizer were dispersed. The third material powder is composed of, for example, 97 wt % zirconia powder, and a total of 3 wt % silica ($SiO_2$) powder and alumina powder, which serve as a sintering conditioner. The plasticizer is composed of a butyral resin and DBP. Using the slurry, the first solid electrolyte member 105 and the second solid electrolyte member 109 were obtained.

Further, for example, 100 wt % alumina powder and a plasticizer were wet-mixed, thereby preparing a slurry in which the powder and the plasticizer were dispersed. The plasticizer is composed of a butyral resin and DBP. Using the slurry, green diffusion-controlling portions 115 of the green insulation layer 107 were obtained as in the case of the second green ceramic sheet 113.

Then, the first green substrate 101, a green heating member 102, the second green substrate 103, a first green electrode 104, a first green solid electrolyte member 105, a second green electrode 106, the green insulation layer 107, a third green electrode 108, a second green solid electrolyte member 109, a fourth green electrode 110, the green protection layer 111, and the like, from bottom to top, were arranged in layers.

Specifically, the green heating member 102 was formed on the first green substrate 101 by a screen printing process using a paste which predominantly contained platinum. Then, the second green substrate 103 was laminated on the first green substrate 101 such that the green heating member 102 was sandwiched therebetween.

The first green electrode 104 was formed on the first green solid electrolyte member 105. The first green electrode 104 is formed from a platinum paste which contains 90 wt % platinum and 10 wt % zirconia powder. The first green electrode 104 was formed by a screen printing process using the platinum paste.

Then, the first green solid electrolyte member 105 was laminated on the second green substrate 103 such that the first green electrode 104 was sandwiched therebetween. Further, the second green electrode 106 was formed, by printing, on the first green solid electrolyte member 105. Material for the second green electrode 106 is similar to that for the first green electrode 104.

Then, the green insulation layer 107 was formed on the second green electrode 106. Specifically, the green insulation portion 114 and the green diffusion-controlling portions 115 were formed. Notably, a paste which predominantly contains carbon is applied to a region of the green insulation layer 107 which will become the gas detection chamber 107c after firing.

Further, the third green electrode 108 was printed on the second green solid electrolyte member 109. The second green solid electrolyte member 109 was laminated on the green insulation layer 107 such that the third green electrode 108 was sandwiched therebetween. Then, the fourth green electrode 110 was printed on the second green solid electrolyte member 109. Material similar to that for the first green electrode 104 is used to form the third green electrode 108 and the fourth green electrode 110. Then, the green protection layer 111 was laminated on the fourth green electrode 110.

The resultant multilayer article was compression bonded at a pressure of 1 MPa and was then cut to a predetermined size, thereby yielding a laminate. Since the green electrode protection member 113a was pressed in the pressing step, the laminate is such that the gap G is unlikely to arise between the green reinforcement member 112 and the green electrode protection member 113a as shown in FIG. 8.

Subsequently, the laminate is fired. Specifically, the laminate undergoes resin removal firing, and is then subjected to main firing, thereby yielding the gas sensor element 300 for detecting the concentration of oxygen in exhaust gas.

When the firing step is performed, the first green electrode 104 becomes the first electrode 104 which includes the first electrode portion 104a and the first lead portion 104b. The first green solid electrolyte member 105 becomes the first solid electrolyte member 105. The second green electrode 106 becomes the second electrode 106 which includes the second electrode portion 106a and the second lead portion 106b. The green insulation portion 114 of the green insulation layer 107 becomes the insulation portion 114, and the green diffusion-controlling portions 115 of the green insulation layer 107 become the porous diffusion-controlling portions 115. In this manner, the green insulation layer 107 becomes the insulation layer 107. The gas detection chamber 107c of the insulation layer 107 communicates with the outside via the diffusion-controlling portion 115 located at laterally opposite sides of the insulation portion 114. The diffusion-controlling portions 115 implement gas diffusion at a predetermined flow rate between the outside and the gas detection chamber 107c. The third green electrode 108 becomes the third electrode 108 which includes the third electrode portion 108a and the third lead portion 108b. The second green solid electrolyte member 109 becomes the second solid electrolyte member 109. The fourth green electrode 110 becomes the fourth electrode 110 which includes the fourth electrode portion 110a and the fourth lead portion 110b. The green reinforcement member 112 of the green protection layer 111 becomes the reinforcement member 112 for protecting the second solid electrolyte member 109, and the green electrode protection member 113a of the green protection layer 111 becomes the porous electrode protection member 113a for protecting the fourth green electrode 110 from poisoning.

Particularly, the method for manufacturing the gas sensor element 300 employs a laminate in which the gap G is unlikely to arise between the green reinforcement member 112 and the green electrode protection member 113a as shown in FIG. 8. Thus, thermal shrinkage of the second green solid electrolyte member 109 during the firing step in becoming the second solid electrolyte member 109 is unlikely to be influenced by an atmosphere which would otherwise be present in the gap G formed in a conventional manufacturing method. As such, a crack CR is unlikely to be initiated in the second solid electrolyte member 109. Also, the reinforcement member 112 is substantially identical in thickness to the electrode protection member 113a.

Since the electrode protection member 113a which is formed through firing while being fitted in the insertion hole 112a of the green reinforcement member 112 in a gapless condition does not have a sharp corner as viewed in the laminating direction, thermal strength and mechanical strength are enhanced.

As shown in FIG. 9, the metallic shell 23, the external tube 25, the protector 24, and the like are prepared and assembled together, thereby yielding a gas sensor. In the gas sensor, since the crack CR is unlikely to be initiated in the second solid electrolyte member 109 of the gas sensor element 300, the electric potential between the electrodes developed by a gas to be measured is not lowered. Thus, variation in gas detection performance among respective gas sensors becomes small. Also, the inventive gas sensors are manufactured in high yield.

Figure 10:
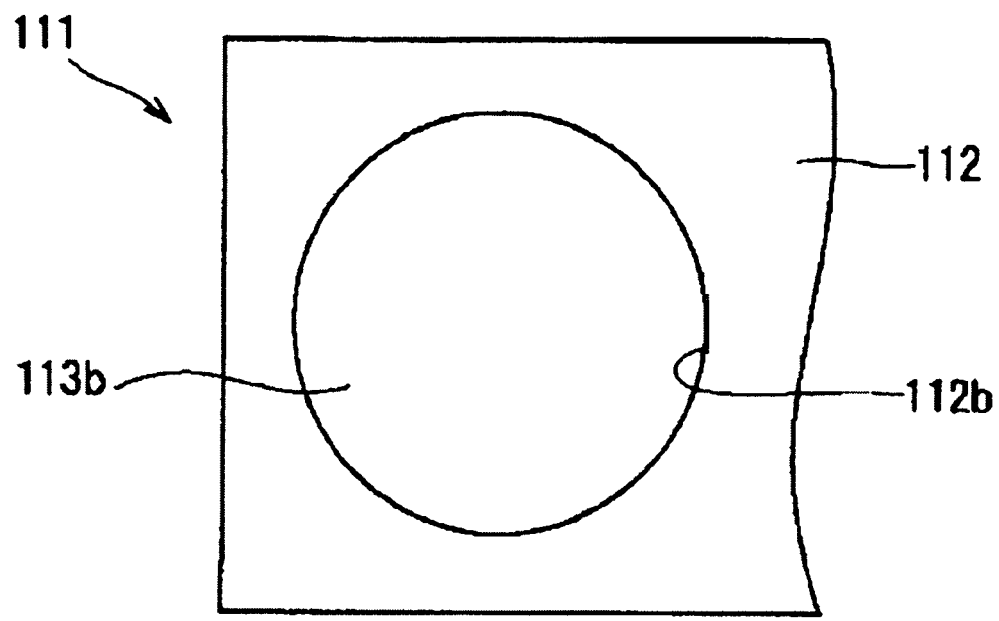
FIG. 10 is a plan view relating to a modified embodiment and showing a green protection layer including a green reinforcement member and a green electrode protection member.

As shown in FIG. 10, an insertion hole 112b which has a circular shape as viewed in the vertical direction can be formed in the green reinforcement member 112 of the green protection layer 111, and a green electrode protection member 113b can be fitted into the insertion hole 112b. In addition to a circular shape, the insertion hole can be adapted to have a square shape having rounded corners, a rectangular shape having rounded corners, an elliptical shape, or a like shape, and a corresponding green electrode protection member can be fitted into such an insertion hole.

Embodiment 2

Figure 12:
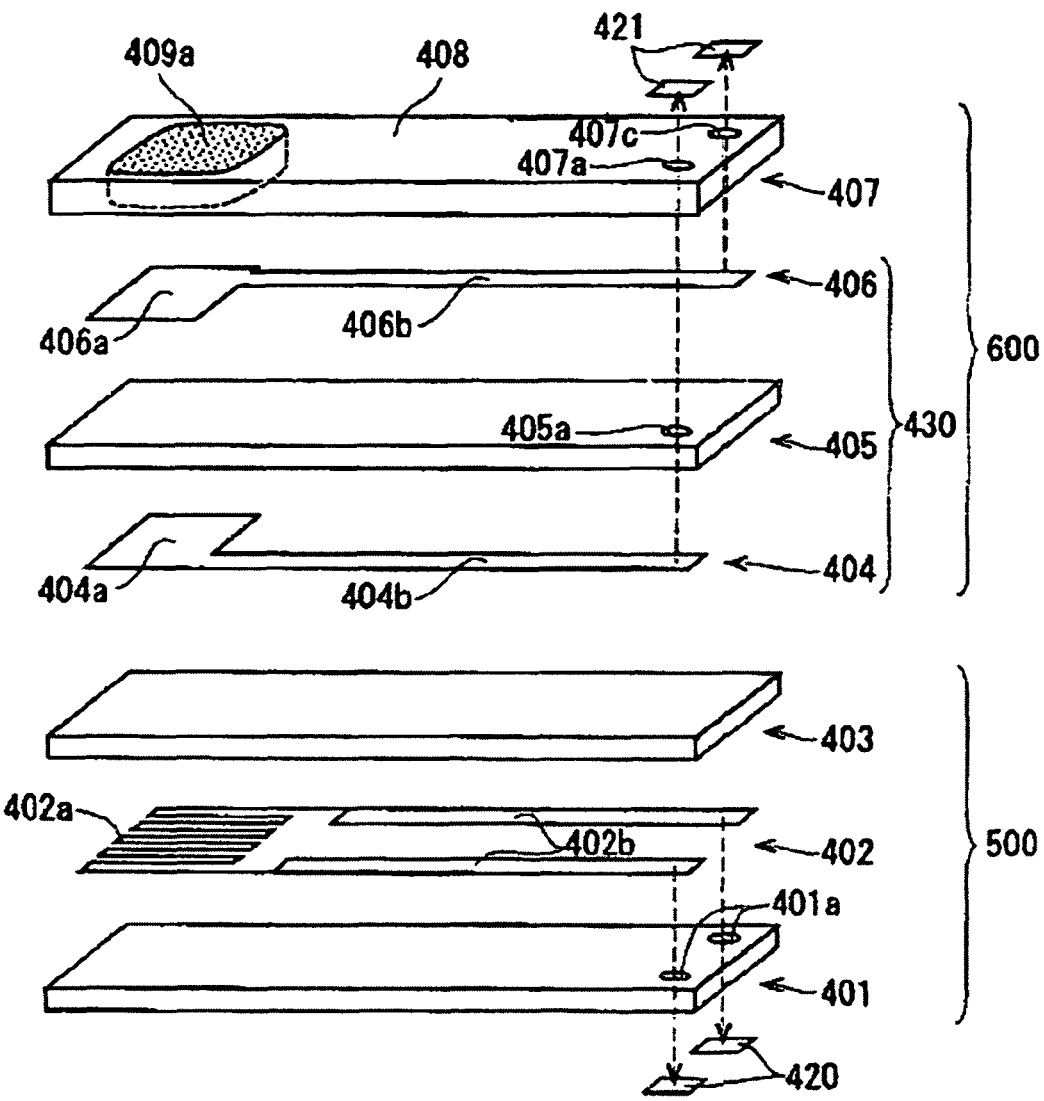
FIG. 12 is a schematic exploded perspective view of a gas sensor element and a heater according to Embodiment 2.
Figure 13:
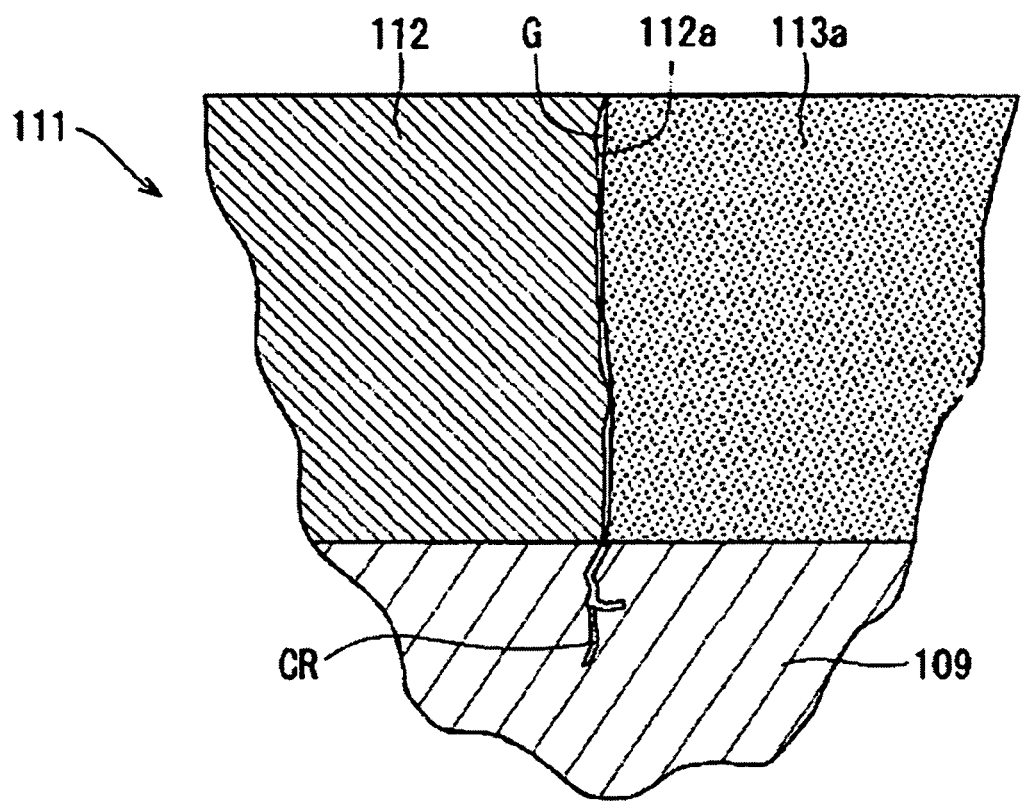
FIG. 13 is a schematic enlarged sectional view of a conventional gas sensor element.

The gas sensor of Embodiment 2 is similar to that of Embodiment 1. In Embodiment 1, the gas sensor element 300 shown in FIG. 11 is fabricated to have the oxygen concentration detection cell 130, the insulation layer 107, the oxygen pump cell 140, and the protection layer 111. A gas sensor element 600 of Embodiment 2 shown in FIG. 12 and having an oxygen concentration detection cell 430 and a protection layer 407 can be manufactured in a similar manner.

The gas sensor element 600 of Embodiment 2, together with a heater 500, will next be described. The gas sensor element 600 does not have an oxygen pump cell and an insulation layer. Other structural features will be described using corresponding terms of Embodiment 1.

The heater 500 includes a first substrate 401, a second substrate 403, and a heating member 402. The first and second substrates 401 and 403 predominantly contain alumina, and the heating member 402 is sandwiched between the first and second substrates 401 and 403. The heating member 402 includes a heating portion 402a and a pair of heater lead portions 402b. Ends of the heater lead portions 402b are electrically connected to corresponding heater-side pads 420 via corresponding through holes 401a.

The oxygen concentration detection cell 430 of the gas sensor element 600 includes a first solid electrolyte member 405, a first electrode 404, and a second electrode 406. The first and second electrodes 404 and 406 are formed on corresponding opposite sides of the first solid electrolyte member 405. The first electrode 404 includes a first electrode portion 404a and a first lead portion 404b. The second electrode 406 includes a second electrode portion 406a and a second lead portion 406b.

An end of the first lead portion 404b is electrically connected to a corresponding gas-sensor-element-side pad 421 via a through hole 405a and a through hole 407a. An end of the second lead portion 406b is electrically connected to a corresponding gas-sensor-element-side pad 421 via a through hole 407c.

The first solid electrolyte member 405 is made of a partially-stabilized-zirconia sintered body which is formed by adding yttria ($Y_2O_3$) or calcia (CaO) serving as a stabilizer to zirconia ($ZrO_2$).

The heating member 402, the first electrode 404, the second electrode 406, the heater-side pads 420, and the gas-sensor-element-side pads 421 can be formed from a platinum group element. Platinum group elements which are preferred for forming the members include Pt, Rh, and Pd. These elements can be used singly or in combination.

A protection layer 407 is formed on the surface of the first solid electrolyte member 405 such that the second electrode 406 is sandwiched therebetween. The protection layer 407 includes a porous electrode protection member 409a and a reinforcement member 408. The electrode protection member 409a is arranged so as to cover the second electrode portion 406a and is adapted to protect the second electrode portion 406a from becoming poisoned. The reinforcement member 408 protects the first solid electrolyte member 405 and is positioned such that the second lead portion 406b is sandwiched therebetween.

The thus-configured gas sensor element 600 can be manufactured in a manner similar to that of Embodiment 1, and can be used in the gas sensor shown in FIG. 9. In such application, the gas sensor element 600 yields similar action and effects as does the gas sensor element of Embodiment 1.

While the present invention has been described with reference to Embodiments 1 and 2, the present invention is not limited thereto, but may be modified as appropriate without departing from the spirit and scope of the invention.

For example, in Embodiments 1 and 2, a material which predominantly contains alumina is used to form the first substrates 101 and 401 and the second substrates 103 and 403. However, the present invention is not limited thereto. A material which predominantly contains zirconia may be used.

Also, in Embodiment 1, a material which predominantly contains alumina is used to form the insulation portion 114 of the insulation layer 107. However, the present invention is not limited thereto. A material which predominantly contains zirconia may be used.

In Embodiment 2, the heater 500 and the gas sensor element 600 are arranged in layers while being in direct contact with each other. However, the present invention is not limited thereto. A layer which has an atmosphere introduction hole for exposing the first electrode 404 to the atmosphere may intervene therebetween.

In the pressing step of Embodiment 1, a single forming die P1 is used to cut the insertion hole 112a through the green reinforcement member 112 and to insert the green electrode protection member 113 into the insertion hole 112a. However, the present invention is not limited thereto. Alternatively, the pressing step may be conducted as follows. After the insertion hole 112a is cut through the green reinforcement member 112, the green reinforcement member 112 is unloaded. The green reinforcement member 112 is placed on a forming die whose lower die does not have the working hole 1a. Then, the green electrode protection layer 113 is inserted into the insertion hole 112a.

INDUSTRIAL APPLICABILITY

The gas sensor element and the gas sensor according to the present invention can be widely used in engines, exhaust gas sensors (oxygen sensors, hydrocarbon sensors, $NO_x$ sensors, etc.), and other various kinds of sensors.

This application is based on Japanese Patent Application No. 2005-100425 filed Mar. 31, 2005, incorporated herein by reference in its entirety.

What is claimed is:

1. A method for manufacturing a gas sensor element comprising a solid electrolyte member, an electrode formed on the solid electrolyte member, and a protection layer including a reinforcement member having an insertion hole, and a porous electrode protection member provided in the insertion hole and adapted to protect the electrode from becoming poisoned, the method comprising:

after disposing a green electrode protection member in the insertion hole of a green reinforcement member, pressing by a die that has a plane that presses both a surface of the green reinforcement member and a surface of the green electrode protection member such that the die presses both the green reinforcement member and the green electrode protection member so as to form a green protection layer;

next arranging the green protection layer and a green solid electrolyte member in layers so as to form a laminate which will become the gas sensor element after being fired; and after the arranging step, firing the laminate, wherein before the pressing step is performed, the green electrode protection member has a thickness greater than that of the green reinforcement member, and wherein the reinforcement member and the electrode protection member have substantially the same thickness.

2. The method for manufacturing a gas sensor element according to claim 1, which comprises carrying out the pressing step at room temperature or higher.

3. The method for manufacturing a gas sensor element according to claim 1, wherein the insertion hole does not have a sharp corner.

4. A method for manufacturing a gas sensor element comprising a solid electrolyte member having a plate-like shape, an electrode formed on the solid electrolyte member, and a protection layer including a reinforcement member having an insertion hole, and a porous electrode protection member provided in the insertion hole and adapted to protect the electrode from becoming poisoned, the method comprising:

punching the insertion hole in a first green ceramic sheet so as to form a green reinforcement member having the insertion hole;

placing a second green ceramic sheet in direct contact on the green reinforcement member, the second green ceramic sheet having a thickness greater than that of the first green ceramic sheet;

blanking out a blank from the second green ceramic sheet so as to dispose the blank as a green electrode protection member in the insertion hole of the green reinforcement member, the green electrode protection member having a thickness greater than that of the green reinforcement member; and firing the green reinforcement member and the green electrode protection member so as to form the reinforcement member and the electrode protection member.

5. The method for manufacturing a gas sensor element according to claim 4, which further comprises, after the blanking step, pressing by a die that has a plane that presses a surface of the green electrode protection member such that the die presses the green electrode protection member so as to form a green protection layer.

* * * * *